United States Patent [19]
Stubbs

[11] Patent Number: 5,842,974
[45] Date of Patent: Dec. 1, 1998

[54] ARCADE SPECULUM AND METHOD OF USE

[76] Inventor: R. Clay Stubbs, Rte. 2, Box 18, Spicewood, Tex. 78669

[21] Appl. No.: 944,859

[22] Filed: Oct. 6, 1997

Related U.S. Application Data

[60] Provisional application No. 60/044,396 Apr. 29, 1997.
[51] Int. Cl.⁶ .................................................. A61B 17/00
[52] U.S. Cl. .......................... 600/206; 600/209; 600/243; 600/237; 600/235
[58] Field of Search ..................................... 600/184, 201, 600/206, 209, 211, 235, 237, 238, 239, 240, 241, 242, 243, 245

[56] References Cited

U.S. PATENT DOCUMENTS

| | | | |
|---|---|---|---|
| 776,348 | 11/1904 | Parsons | 600/242 X |
| 779,885 | 1/1905 | Spangler | 600/209 |
| 922,078 | 5/1909 | Benson | 600/241 |
| 2,382,385 | 8/1945 | Condit | 600/240 X |
| 2,581,679 | 1/1952 | Marshall . | |

*Primary Examiner*—Jeffrey A. Smith
*Attorney, Agent, or Firm*—Ted Masters

[57] ABSTRACT

A speculum (20) for obtaining visual access to the inside of an animal's (500) mouth includes a body (22), and handle (28) and two spaced loop-shaped members (30) and (32). Loop-shaped members (30) and (32) have arcuate ends (34) and (36) which individually or in unison may be hooked around the last jaw teeth (502) through (505), while speculum (20) is selectively manipulated by handle (28) to allow visual access to the animal's (500) teeth (501), tongue (506), cheeks (507) and (508), and soft mouth tissue (509). Speculum (20) is fabricated from a rod-like material to ensure maximum visibility by the using veterinarian.

15 Claims, 6 Drawing Sheets

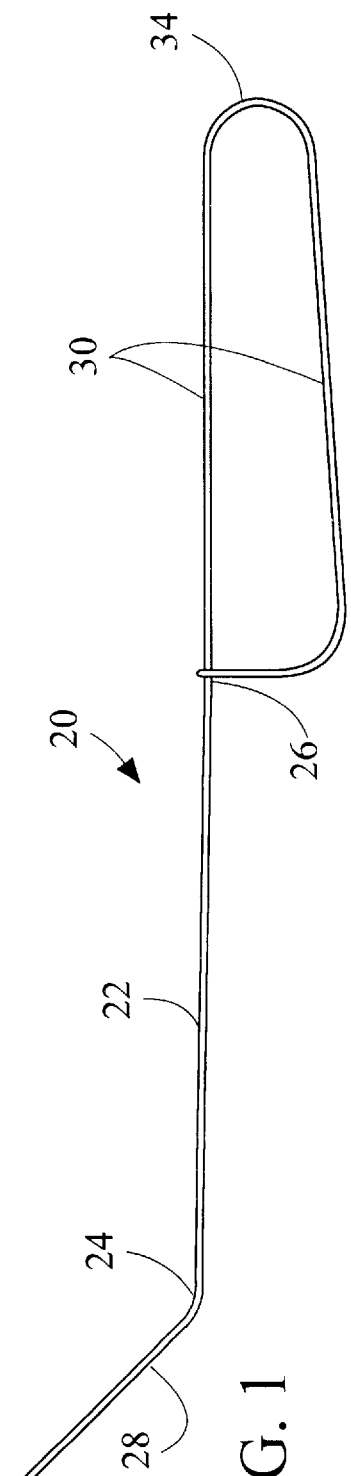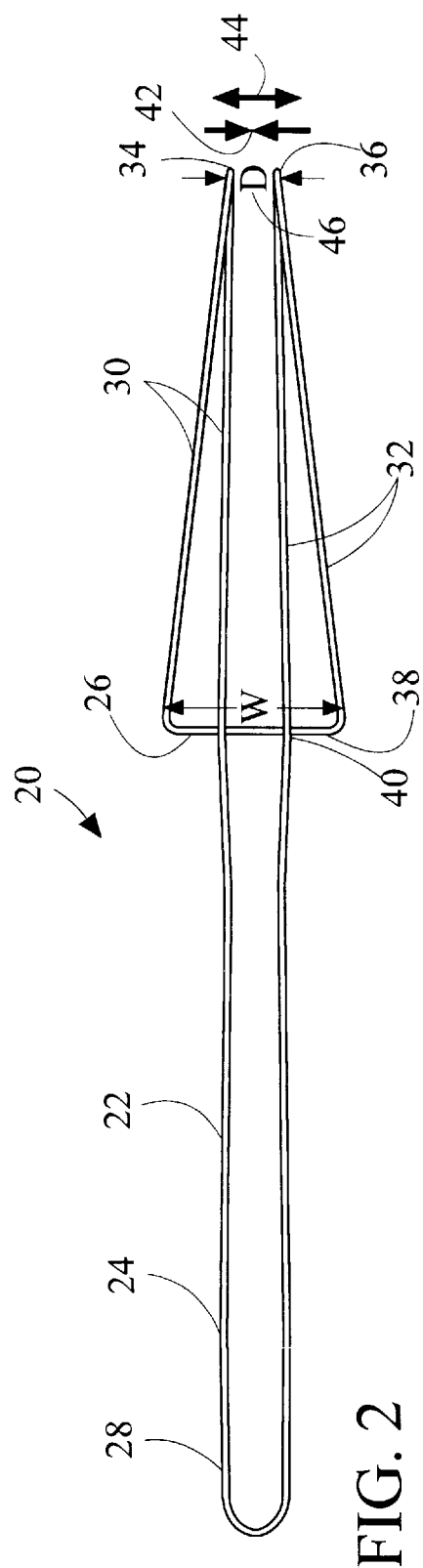

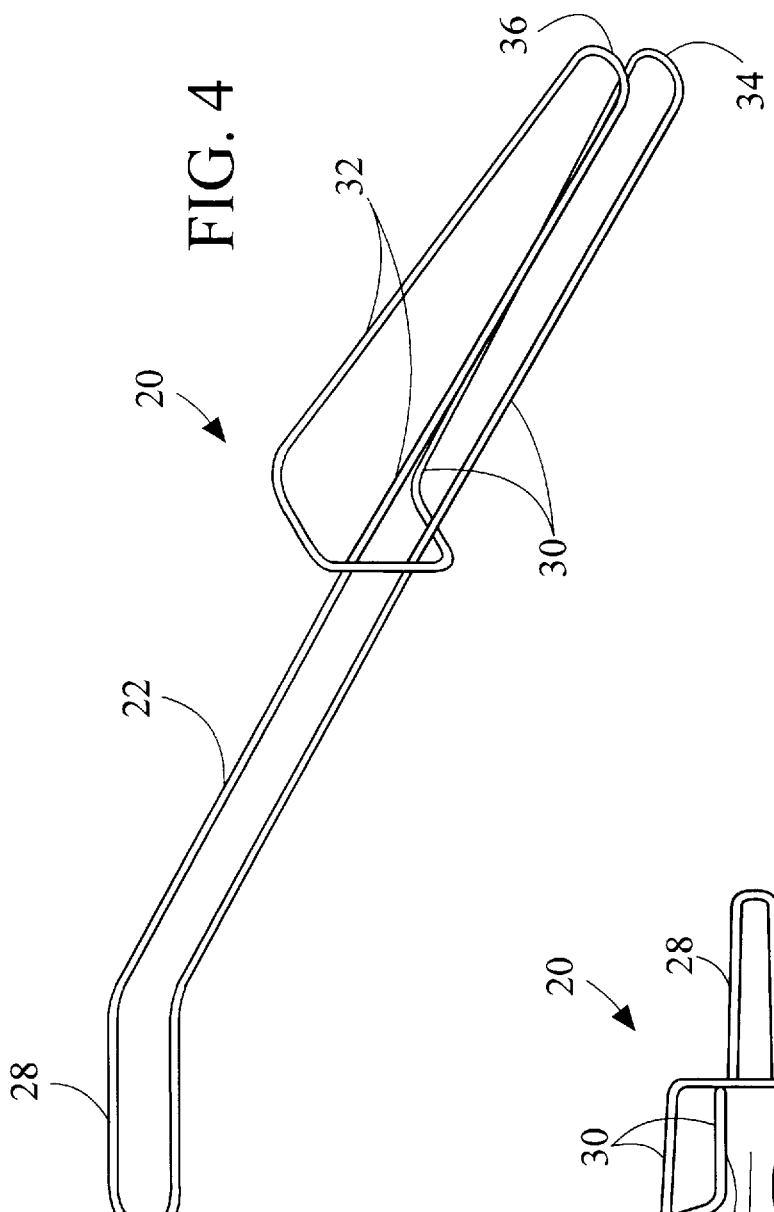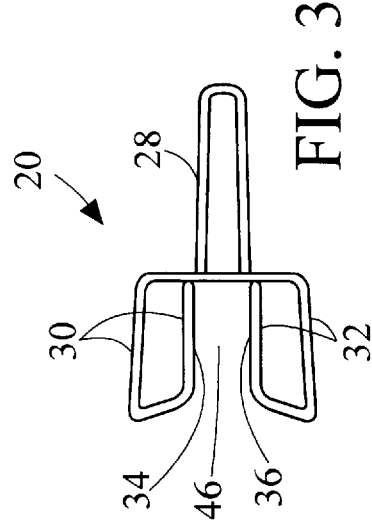

ARCADE SPECULUM AND METHOD OF USE

CROSS REFERENCE TO RELATED APPLICATION

This application claims the benefit of 35 U.S.C. §119(e) of U.S. Provisional Application No. 60/044,396, filed Apr. 29, 1997.

TECHNICAL FIELD

The present invention pertains to devices which are used to provide visual access to the inside of an animal's mouth for veterinary purposes.

BACKGROUND ART

Specula and the like for viewing the inside of an animal's mouth are well known in the art. These devices are typically positioned between the upper and lower jaws of the animal, and manipulated in order to provide visual access to the desired area. In so doing, access to the mouth and teeth is obtained for the purposes of examination and medical procedures. For example, U.S. Pat. No. 404,652 shows a veterinary mouth speculum for a horse or other animal. The device holds the jaws of the animal in an open position for veterinary purposes. Two jaw pieces are pivotally connected to the ends of two arms. The two arms are connected to opposite ends of a handle which can be selectively rotated to increase or decrease the distance between the jaw pieces. U.S. Pat. No. 585,101 defines a veterinary mouth speculum having a supporting bow or yoke of essentially semicircular shape. The two ends of the bow are connected to upper and lower jaws respectively by ratchet mechanisms. The upper and lower jaws of the speculum are placed around the upper and lower jaws of the animal, and the ratchet mechanisms are utilized to retain the animal's jaws in the desired open position. U.S. Pat. No. 2,516,413 depicts an apparatus for treating meteorism or tympanites in animals, particularly horned cattle. The apparatus includes two members forming first class levers which are joined in a scissor-like manner. A spring urges the levers into an open position, thereby forcing the animal to open its mouth. U.S. Pat. No. 2,581,679 discloses a device for the relief of bloat in cattle. The device includes a bit-like metal or plastic frame, which is secured in place in the animal's mouth and remains in position until the condition of bloat is fully relieved. U.S. Pat. No. 2,587,245 comprises a combined mouth speculum and tongue support. A main mouth prop or post is bifurcated longitudinally so as to receive a rod which carries a tongue support. The rod is mounted on a slidable sleeve which is adjustable in any conceivable position lengthwise of the prop. U.S. Pat. No. 2,844,142 consists of a device for constraining the tongue. The device comprises a pair of loops, of different size, the smaller of the loops being pendently supported within the larger loop and being, comprised of an elastic substance. U.S. Pat. No. 3,734,084 describes a mechanical tongue depressor having a laterally offset clamp which enables it to be readily clamped to any portion of the vertical post of a conventional mouth speculum wherein the vertical post extends between the upper and lower jaws of the mouth alongside the mouth cavity. U.S. Pat. No. 4,450,831 includes a self supporting mouth speculum for horses, mules, and other animals. The speculum has first and second cheek hooks adjustably connected together by a pair of straps extending therebetween.

DISCLOSURE OF INVENTION

The present invention comprises an arcade speculum which is designed to allow observation of the jaw teeth, tongue, cheeks, and soft mouth tissue of an animal, and in particular to a horse or other member of the equine species. Due to the anatomy and the depth of the horse's mouth, visualization has typically heretofore been difficult or impossible, because when the mouth is held open with a full mouth speculum, the tongue and cheeks obstruct the view of the back teeth. The present invention spreads the cheeks laterally and the tongue medially so that the jaw teeth and surrounding soft mouth tissue can be observed. This is important because sharp protrusions from the teeth can abrade and damage the soft mouth tissue and create ulcers. If not corrected by rasping the offending teeth, this condition can cause the animal considerable pain and discomfort. The present invention allows visual access to uncover this and other problems within the animals mouth.

In accordance with a preferred embodiment of the invention, the speculum has a body having a first end and an opposite second end. A handle is connected to the first end. A first loop-shaped member having a first arcuate end for attachment around one of the last jaw teeth, and an opposite second end, is connected to the second end of the body. A second loop-shaped member having a second arcuate end for attachment around one of the last jaw teeth, and an opposite second end, is also connected to the second end of said body. The second arcuate end of the second loop-shaped member is substantially parallel to and spaced a predetermined distance from the first arcuate end of the first loop-shaped member, thereby forming an opening therebetween. The first and second loop-shaped members are fabricated from a rod-like material.

In accordance with an important aspect of the invention, the first and second loop-shaped members are flexible so that they can resiliently move both toward and away from each other.

In accordance with an important feature of the invention, the first and second loop-shaped members are malleable so that said predetermined distance may be selectively changed.

In accordance with another important aspect of the invention, the rod-like material has a substantially circular cross section.

In accordance with another feature of the invention, the rod-like material is corrosion-resistant.

In accordance with an aspect of the invention, the handle forms an obtuse angle with said body.

In accordance with a feature of the invention, a flashlight is attached to the body, and directed toward the first and second arcuate ends.

Other features and advantages of the present invention will become apparent from the following detailed description, taken in conjunction with the accompanying drawings, which illustrate, by way of examples, the principles of the invention.

BRIEF DESCRIPTION OF DRAWINGS

FIG. 1 is a top plan view of an arcade speculum in accordance with the present invention;

FIG. 2 is a side elevation view of the speculum;

FIG. 3 is a front elevation view of the speculum;

FIG. 4 is an inverted perspective view of the speculum;

MODES FOR CARRYING OUT THE INVENTION

Figure 5:
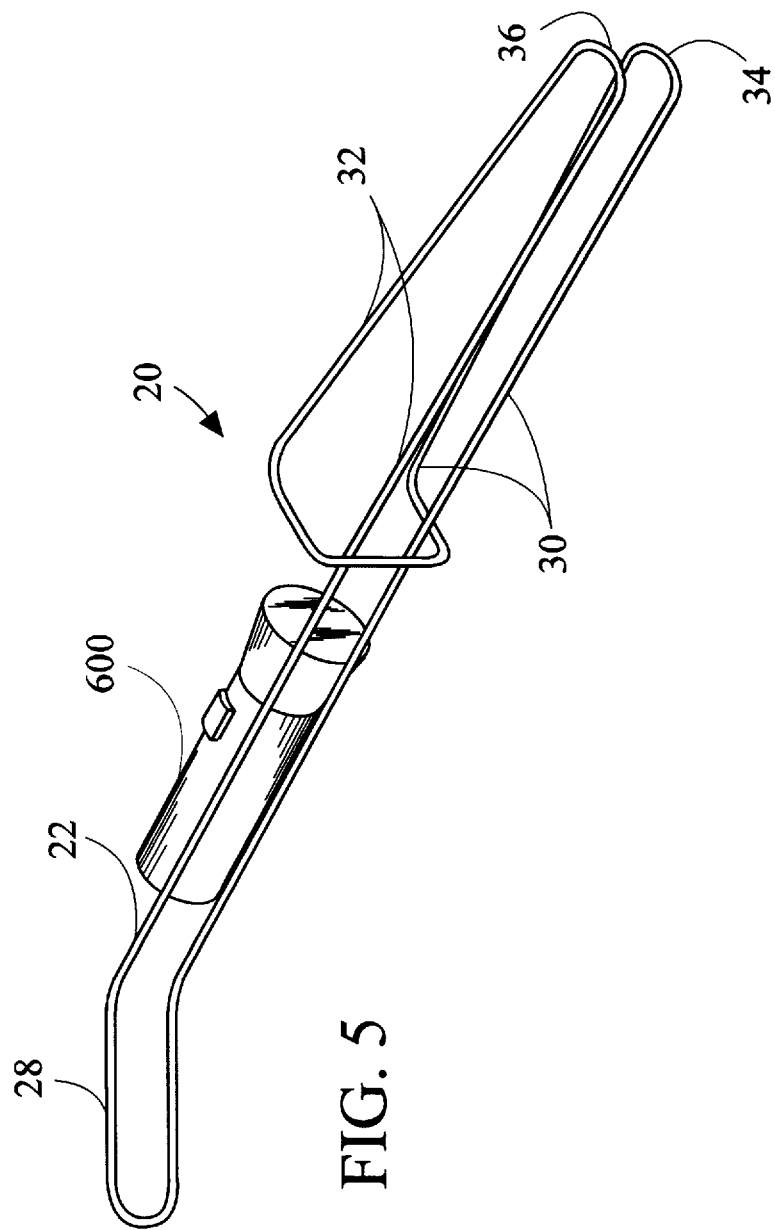
FIG. 5 is an inverted perspective view of the speculum with a flashlight attached.

Referring initially to FIGS. 1–4, there are illustrated top plan, side elevation, front elevation, and inverted perspective views respectively, of a speculum for animals in accordance with the present invention, generally designated as 20. Speculum 20 is specifically designed to provide visual access to the inside of animal's 500 mouths wherein the inside of the mouth includes teeth 501 with a plurality of last jaw teeth 502 thorough 505, a tongue 506, two cheeks 507 and 508, and soft mouth tissue 509.(refer also to FIGS. 6, 7, and 8) Speculum 20 includes a body 22 having a first end 24 and an opposite second end 26. A handle 28 is connected to first end 24. Handle 28 forms an obtuse angle with body 22 to allow easier manipulation with one hand. A first loop-shaped member 30 has a first arcuate end 34 for attachment around one of the last jaw teeth 502 through 505. Arcuate end 34 is sized to receive one of the last jaw teeth 502 through 505. Additionally, by curving first arcuate end 34, speculum 20 does not traumatize or injure the animal 500 when it is inserted into and moved about within the mouth. First loop-shaped member 30 also has an opposite second end 38 which is connected to second end 26 of body 22.

A second loop-shaped member 32 has a second arcuate end 36, also sized for attachment around one of the last jaw teeth 502 through 505. Second loop-shaped member 32 also has an opposite end 40 which is connected to second end 26 of body 22. Second arcuate end 36 of second loop-shaped member 32 is substantially parallel to and spaced a predetermined distance D from first arcuate end 34 of first loop-shaped member 30, and forms an opening 46 therebetween. Two spaced loop-shaped members 30 and 32 are flexible so that they can resiliently move toward or away from each other in directions 42 and 44 respectively. The flexibility allows the two arcuate ends 34 and 36 to compress and resiliently move toward one another, thereby permitting access to small spaces within the animal's 500 mouth. Two spaced loop-shaped members 30 and 32 are also malleable so that first 34 and second 36 arcuate ends can be permanently moved toward or away from each other thereby selectively changing predetermined distance D. This permits the opening 46 between the two arcuate ends 34 and 36 to be selectively adjusted to accommodate different size mouths.

Speculum 20, including first 30 and second 32 loop-shaped members, is fabricated from rod-like material which results in minimum view obstruction. In a preferred embodiment, the rod-like material has a substantially circular cross section which is less likely to harm the animal 500. In a preferred embodiment, the rod-like material is also corrosion-resistant such as stainless steel, which can be easily cleaned and sterilized. Speculum 20 is also preferably light weight so that it can be easily manipulated by the using veterinarian to selectively examine specific small areas in the back of the animal's 500 mouth.

The relatively narrow width W of speculum 20, allows it to be easily inserted and removed through an in-place full mouth speculum. A width W of approximately 3 inches has been found useful. Open space 46 permits an unobstructed view of the inside of the animal's 500 mouth.

FIG. 5 shows speculum 20 with a flashlight 600 attached to body 22, in order to bring light to the dark interior areas of the animal's 500 mouth. Flashlight 600 is directed toward first 34 and second 36 arcuate ends.

Figure 6:
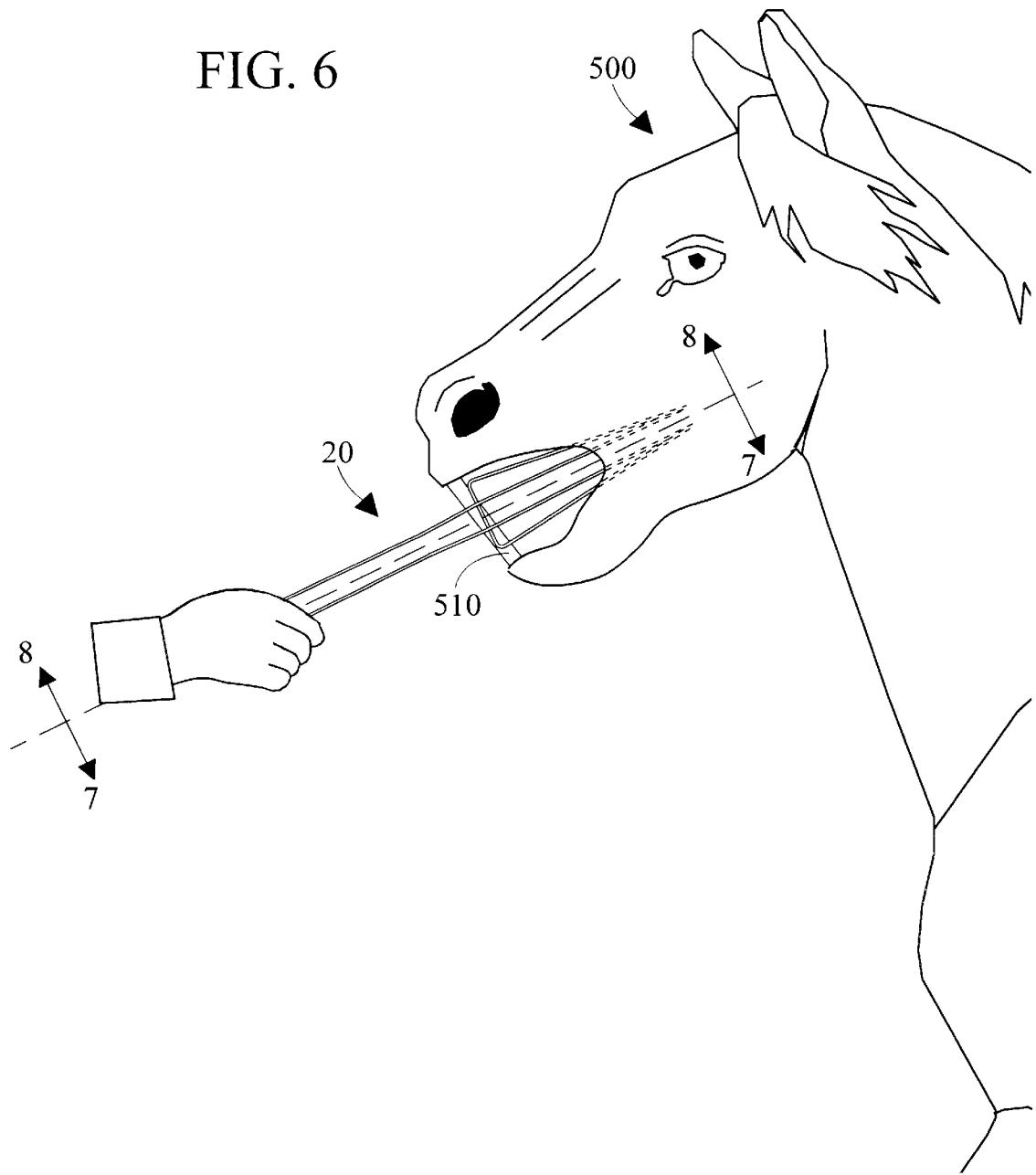
FIG. 6 is a reduced side elevation view of an animal's mouth showing the typical placement and use of the speculum.

FIG. 6 is a reduced side elevation view of an animal's 500 mouth showing the typical placement and use of speculum 20. Speculum 20 has been inserted into the animal's 500 mouth to obtain visual access to the difficult to view back portions. The animal's mouth is usually held open with a full mouth speculum 510 which forces the jaws apart while the arcade speculum 20 of the present invention is being used.

Figure 7:
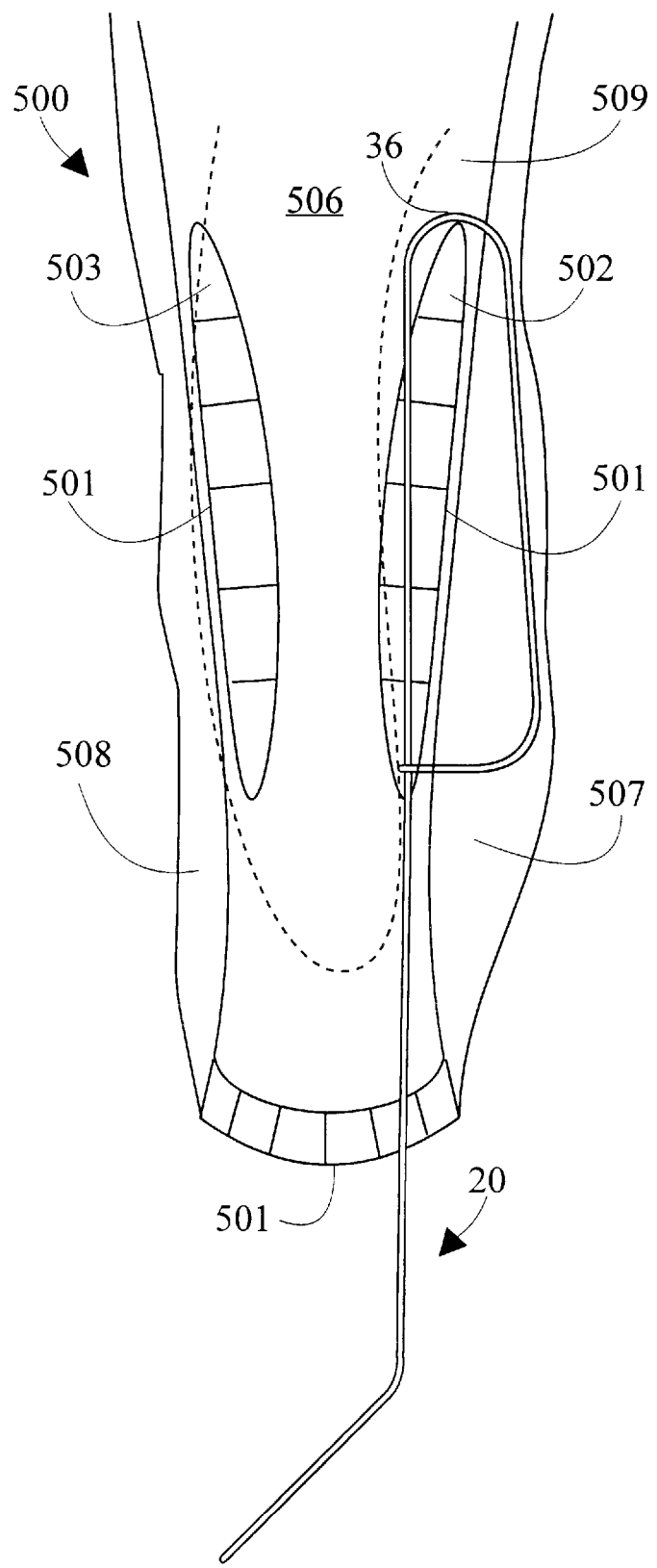
FIG. 7 is a view along the line 7—7 of FIG. 6.
Figure 8:
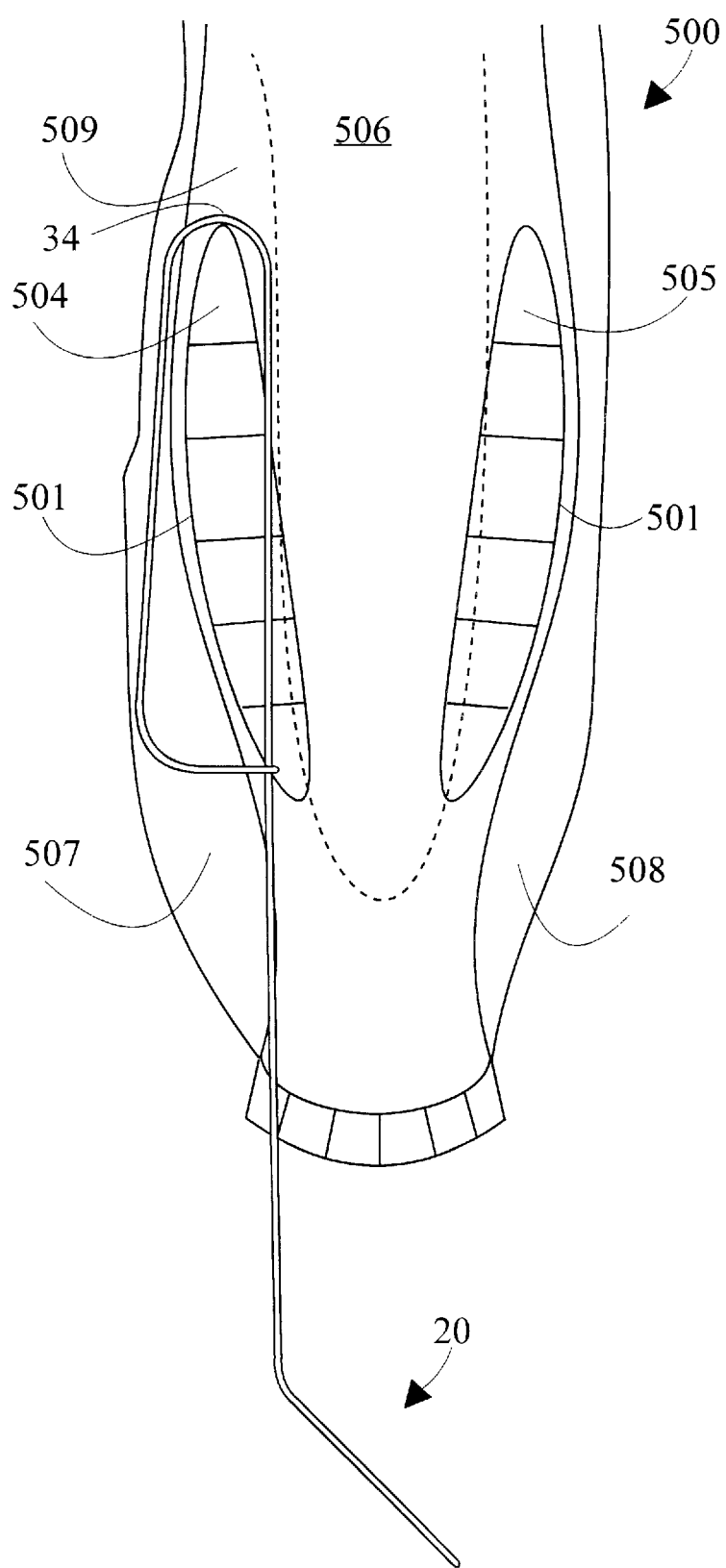
FIG. 8 is a view along the line 8—8 of FIG. 6.

FIG. 7 is a view along the line 7—7 of FIG. 6, and shows speculum 20 with respect to the animal's 500 lower jaw, and FIG. 8 is a view along the line 8—8 of FIG. 6, and shows speculum 20 with respect to the animal's upper jaw. Arcuate ends 34 and 36 are then attached (hooked or anchored) around the last jaw teeth 504 and 502. First arcuate end 34 is attached (hooked) around the last upper jaw tooth 504, and second arcuate end 36 is hooked around the last lower jaw tooth 502. It is noted that The attachment can also be reversed wherein first arcuate end 34 is attached around the last lower jaw tooth 502, and the second arcuate end 36 attached around the last upper jaw tooth 504. It is noted that either one arcuate end or both arcuate ends can be attached. With at least one of the two arcuate ends 34 and 36 anchored around the jaw teeth 504 and 502 respectively, using handle 28 the veterinarian can selectively manipulate speculum 20 by twisting, pushing, and pulling up, down, to the right, or to the left to obtain visual access to the animal's 500 teeth 501, last jaw teeth 502 and 504, tongue 506, cheeks 507 and 508, and soft mouth tissue 509 all the way forward to the animal's 500 lips. Of course speculum 20 may be place on the opposite side of the animal's 500 mouth and be hooked around last jaw teeth 503 and 505. Speculum 20 is also very useful in flattening or otherwise positioning the animal's tongue 506.

Speculum 20 is particularly useful because as the mouth of the animal 500 is opened with a full mouth speculum 510, the animal's cheeks 507 and 508 stretch over the teeth 501 making observation difficult. This situation is compounded by the animal's 500 tongue 506 which can further obstruct visual access. By attaching flashlight 600 to body 22 of speculum 20 and turning the flashlight 600 on, the veterinarian can use his/her other hand (one hand is holding handle 28 of speculum 20) to pull on the end of tongue 506 so as to move it out of the way and illuminate the inside of the animal's 500 mouth. The resilient action of arcuate ends 34 and 36 allows speculum 20 to snap in place over the last jaw teeth 502 and 504 or 503 and 505, and hold the animal's cheeks 507 and 508, and tongue 506 away from its teeth 501, by spreading the tongue 506 medially away from the teeth 501, and spreading the cheeks 507 and 508 laterally also away from the teeth 501. In this position, speculum 20 allows observation of and re-observation of the soft tissue that the animal can continuously move.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A speculum for an animal having teeth including a plurality of last jaw teeth, comprising:

a body having a first end and an opposite second end;

a handle connected to said first end;

a first loop-shaped member having a first arcuate end for attachment around one of the last jaw teeth, and an opposite second end, said second end connected to said second end of said body;

a second loop-shaped member having a second arcuate end for attachment around one of the last jaw teeth, and an opposite second end, said second end connected to said second end of said body, said second arcuate end of said second loop-shaped member substantially parallel to and spaced a predetermined distance from said first arcuate end of said first loop-shaped member, thereby forming an opening therebetween; and, said first and second loop-shaped members fabricated from a rod-like material.

2. A speculum according to claim 1, wherein said first and second loop-shaped members are flexible so that they can resiliently move both toward and away from each other.

3. A speculum according to claim 1, wherein said first and second loop-shaped members are malleable so that said predetermined distance may be selectively changed.

4. A speculum according to claim 1, wherein said rod-like material has a substantially circular cross section.

5. A speculum according to claim 1, wherein said rod-like material is corrosion-resistant.

6. A speculum according to claim 1, wherein said handle forms an obtuse angle with said body.

7. A speculum according to claim 1, further including a flashlight attached to said body, said flashlight directed toward said first and second arcuate ends.

8. A speculum according to claim 1, further including:

said first and second loop-shaped members being flexible so that they can resiliently move both toward and away from each other;

said first and second loop-shaped members being malleable so that said predetermined distance may be selectively changed; and, said rod-like material having a substantially circular cross section.

9. A method for examining the mouth of an animal, the animal having teeth including a plurality of last jaw teeth, a tongue, cheeks, and soft mouth tissue, comprising the steps of:

providing an arcade speculum having a body having a first end and an opposite second end, a handle connected to said first end, a first loop-shaped member having a first arcuate end for attachment around one of the last jaw teeth, and an opposite second end, said second end connected to said second end of said body, a second loop-shaped member having a second arcuate end for attachment around one of the last jaw teeth, and an opposite second end, said second end connected to said second end of said body, said first arcuate end substantially parallel to and spaced a predetermined distance from said second arcuate end, thereby forming an opening therebetween, said first and second loop-shaped members fabricated from a rod-like material, said first and second loop-shaped members being flexible so that they can resiliently move both toward and away from each other, and said first and second loop-shaped members being malleable so that said predetermined distance may be selectively changed;

providing a full-mouth speculum;

installing the full-mouth speculum in the animal's mouth;

inserting said arcade speculum into the animal's mouth;

attaching at least one of said first and second arcuate ends around the last jaw teeth;

using said handle to selectively manipulate said arcade speculum to allow visual access to the animal's teeth, tongue, cheeks, and soft mouth tissue.

10. The method according to claim 9, further including the step of:

attaching both of said first and second arcuate ends around the two last jaw teeth on the same side of the animal's mouth.

11. The method according to claim 9, further including the step of:

selectively adjusting said predetermined distance.

12. The method according to claim 9, further including the steps of:

providing a flashlight;

attaching the flashlight to said body so that the flashlight is directed at said first and second arcuate ends;

turning on the flashlight so that it illuminates the inside of the animal's mouth.

13. The method according to claim 9, further including the step of:

using said arcade speculum to flatten or otherwise position the animal's tongue.

14. The method according to claim 9, further including the steps of:

using said arcade speculum to spread the animal's tongue medially away from the teeth;

using said arcade speculum to spread the animal's cheek laterally away from the teeth; and, observing the soft tissue.

15. A method for examining the mouth of an animal, the animal having teeth including a plurality of last jaw teeth, a tongue, cheeks, and soft mouth tissue, comprising the steps of:

providing an arcade speculum having a body having a first end and an opposite second end, a handle connected to said first end, a first loop-shaped member having a first arcuate end for attachment around one of the last jaw teeth, and an opposite second end, said second end connected to said second end of said body, a second loop-shaped member having a second arcuate end for attachment around one of the last jaw teeth, and an opposite second end, said second end connected to said second end of said body, said first arcuate end substantially parallel to and spaced a predetermined distance from said second arcuate end, thereby forming an opening therebetween, said first and second loop-shaped members fabricated from a rod-like material, said first and second loop-shaped members being flexible so that they can resiliently move both toward and away from each other, and said first and second loop-shaped members being malleable so that said predetermined distance may be selectively changed;

providing a full-mouth speculum;

installing the full-mouth speculum in the animal's mouth;

inserting said arcade speculum into the animal's mouth;

forcing said first and second arcuate ends into a small space within the animal's mouth, so that said first and second arcuate ends resiliently move toward each other.

* * * * *